US008827721B2

(12) United States Patent
Totman

(10) Patent No.: US 8,827,721 B2
(45) Date of Patent: Sep. 9, 2014

(54) METHOD OF MEASURING ABDOMINAL THRUSTS FOR CLINICAL USE AND TRAINING

(75) Inventor: Mark H. Totman, Chelmsford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 20 days.

(21) Appl. No.: 13/492,566

(22) Filed: Jun. 8, 2012

(65) Prior Publication Data

US 2013/0330697 A1 Dec. 12, 2013

(51) Int. Cl.
*G09B 23/28* (2006.01)
*A61B 5/00* (2006.01)

(52) U.S. Cl.
CPC .................. *A61B 5/0006* (2013.01)
USPC ........... 434/275; 434/262; 434/265; 600/300; 601/41

(58) Field of Classification Search
CPC ...... G09B 23/30; G09B 23/32; A61B 5/0002; G06F 19/3406
USPC .................... 434/262, 263, 265, 275; 600/301
See application file for complete search history.

(56) References Cited

U.S. PATENT DOCUMENTS

| | | | |
|---|---|---|---|
| 443,204 A | 12/1890 | Davis | |
| 651,962 A | 6/1900 | Boghean | |
| 2,071,215 A | 2/1937 | Petersen | |
| 2,486,667 A | 11/1949 | Meister | |
| RE26,511 E | 12/1968 | Hewson | |
| 3,568,078 A | 3/1971 | Pelchat | |
| 4,424,806 A | 1/1984 | Newman et al. | |
| 4,554,910 A | 11/1985 | Lally | |
| 4,676,232 A | 6/1987 | Olsson et al. | |
| 4,770,164 A | 9/1988 | Lach et al. | |
| 4,928,674 A | 5/1990 | Halperin et al. | |
| 4,932,879 A * | 6/1990 | Ingenito et al. | 434/262 |
| 4,987,783 A | 1/1991 | D'antonio et al. | |
| 4,989,611 A | 2/1991 | Zanetti | |
| 5,383,786 A * | 1/1995 | Kohnke | 434/265 |
| 5,423,685 A * | 6/1995 | Adamson et al. | 434/265 |
| 5,453,081 A | 9/1995 | Hansen | |
| 5,490,820 A | 2/1996 | Schock et al. | |
| 5,496,257 A | 3/1996 | Kelly | |
| 5,540,592 A * | 7/1996 | Scheinberg et al. | 434/265 |
| 5,704,365 A | 1/1998 | Albrecht et al. | |
| 5,738,637 A | 4/1998 | Kelly et al. | |
| 5,743,864 A | 4/1998 | Baldwin, II | |
| 5,794,623 A | 8/1998 | Forbes | |
| 5,831,164 A | 11/1998 | Reddi et al. | |
| 5,844,482 A | 12/1998 | Guthrie et al. | |
| 5,876,350 A | 3/1999 | Lo et al. | |
| 5,885,084 A * | 3/1999 | Pastrick et al. | 434/265 |
| 5,913,685 A * | 6/1999 | Hutchins | 434/265 |

(Continued)

OTHER PUBLICATIONS

ProQuest NPL Search Results, May 27, 2014.*

(Continued)

*Primary Examiner* — Nikolai A Gishnock
*Assistant Examiner* — Banafsheh Hadizonooz
(74) *Attorney, Agent, or Firm* — K. David Crockett, Esq.; Paul J. Backofen, Esq.; Crockett & Crockett, PC

(57) ABSTRACT

A method and system for determining the adequacy of abdominal thrusts applied to choking victims during performance of the Heimlich maneuver.

8 Claims, 3 Drawing Sheets

(56) References Cited

U.S. PATENT DOCUMENTS

| | | | |
|---|---|---|---|
| 5,978,693 | A | 11/1999 | Hamilton et al. |
| 6,013,041 | A | 1/2000 | Leathers |
| 6,027,452 | A | 2/2000 | Flaherty et al. |
| 6,174,295 | B1 | 1/2001 | Cantrell et al. |
| 6,179,793 | B1 | 1/2001 | Rothman et al. |
| 6,301,964 | B1 | 10/2001 | Fyfe et al. |
| 6,390,996 | B1 | 5/2002 | Halperin et al. |
| 6,736,643 | B2 * | 5/2004 | Pastrick et al. ............... 434/265 |
| 6,780,017 | B2 * | 8/2004 | Pastrick et al. ............... 434/265 |
| 6,865,413 | B2 | 3/2005 | Halperin et al. |
| 7,074,199 | B2 | 7/2006 | Halperin et al. |
| 7,108,665 | B2 | 9/2006 | Halperin et al. |
| 7,295,871 | B2 | 11/2007 | Halperin et al. |
| 7,429,250 | B2 | 9/2008 | Halperin et al. |
| 2001/0012609 | A1 * | 8/2001 | Pastrick et al. ............... 434/265 |
| 2003/0022142 | A1 * | 1/2003 | Pastrick et al. ............... 434/265 |
| 2004/0115607 | A1 * | 6/2004 | Pastrick et al. ............... 434/262 |
| 2006/0247560 | A1 * | 11/2006 | Halperin et al. ................ 601/41 |
| 2007/0135739 | A1 | 6/2007 | Halperin et al. |
| 2009/0017431 | A1 * | 1/2009 | Adams ......................... 434/265 |
| 2009/0024004 | A1 * | 1/2009 | Yang ............................. 600/301 |
| 2011/0117878 | A1 * | 5/2011 | Barash et al. ............... 455/404.2 |

OTHER PUBLICATIONS

Pinchak, et al., Chest Wall Acceleration and Force Measurement in Simulated and Mechanical CPR, 16 Critical Care Medicine 151 (1988).

Gruben, et al., System for Mechanical Measurements During Cardiopulmonary Resuscitation in Humans, 37 IEEE Trans. on Biomedical Eng. 204(Feb. 1990).

Pinchak, et al., Accelerometer Measurements in CPR, 37th ACEMB 32 (1984).

\* cited by examiner

METHOD OF MEASURING ABDOMINAL THRUSTS FOR CLINICAL USE AND TRAINING

FIELD OF THE INVENTIONS

The inventions described below relate the field of first aid and treatments for choking.

BACKGROUND OF THE INVENTIONS

The Heimlich maneuver is a well-known method of treating choking victims, and refers to a specific technique. The technique requires that a first aid provider grasp the victim from behind, wrap his arms around the victims waist, clasp one hand over the first of the opposite hand, and yank with both hands upwardly and posteriorly into the upper abdomen of the victim, avoiding compression of the rib cage with the arms. This process should dislodge any object obstructing the victim's airway, and may be repeated several times in order to do so.

The abdominal thrusts required for the method should be accomplished abruptly, and should be quite deep. Abdominal thrusts that are too delicate to abruptly pressurize the victim's airway below the lodged obstruction are not effective, but abdominal thrusts that are too deep may unnecessarily injure the victim (in rare instances, the injury may be severe, including rupture of the stomach, fracture of the ribs or xiphoid process, thrombus formation in the aortic aneurysm). It may be difficult for first aid providers to gauge the necessary depth of the abdominal compression, or the speed of compression and level of force needed for a proper abdominal thrust.

Chest compression monitoring during the course of CPR is now possible with the Real CPR Help® technology marketed by ZOLL Medical Corporation. This technology is described in U.S. Pat. Nos. 6,390,996, 7,108,665, and 7,429,250, and includes the use of an accelerometer to measure accelerations of the chest and calculating the depth of each compression from the acceleration signal. The technology is used in ZOLL's Real CPR Help® compression depth monitoring system to provides real-time rate and depth CPR feedback for manual CPR providers. Commercially, it is implemented in ZOLL's electrode pads, such as the CPR-D•Padz® electrode pads. It is also implemented for training use in the iPhone app PocketCPR®. The compression monitor and its method of use can be adapted for use in training and clinical practice of the Heimlich maneuver.

SUMMARY

The devices and methods described below provide for determination of the depth, acceleration, time, speed and force of abdominal thrusts used in the Heimlich maneuver using the compression monitor technology of U.S. Pat. Nos. 6,390,996, 7,108,665, and 7,429,250. The device is modified to provide feedback regarding abdominal thrust parameters to a user. Also, the device is modified such that it determines movement along any vector relative to its housing, so that variations in initial placement and orientation do not effect the measured depth of abdominal thrusts.

DETAILED DESCRIPTION OF THE INVENTIONS

Figure 1:
FIG. 1 illustrates the method of the Heimlich maneuver on a patient by a rescuer holding a compression depth monitor.

FIG. 1 illustrates the method of the Heimlich maneuver on a real patient by a first aid provider holding a compression depth monitor. The victim 1 is standing and conscious, choking on some object lodged in his upper airway. (For training, the victim is replaced with a mannequin.) The first aid provider 2 has wrapped both arms around the victim (or mannequin), balled one hand into a fist, grasped the wrist of that hand with the opposite hand, to prepare to perform the Heimlich maneuver. To accomplish the Heimlich maneuver, the first aid provider pulls abruptly with both hands, yanking upwardly and posteriorly, relative to the victim (or mannequin), on the abdomen. The first aid provider is holding a compression monitor 3 in one hand or the other, or has it attached to the back of one hand or the other or either forearm, or has otherwise secured it to a portion of the first aid provider's hand or wrist which remains in substantially fixed in relation to a surface of the victim's abdomen which is to be compressed, or the first aid provider has fixed it to the surface of the surface of the victim's (or mannequin's) abdomen. (When referring to the mannequin's abdomen, we are referring to that portion of the mannequin that corresponds to the human abdomen.)

The compression monitor is operated by the first aid provider to detect the abdominal thrust and report on its parameters. The parameters may include the depth and speed of the thrust, the acceleration of the thrust and the length of time that acceleration is applied, and these can be determined using accelerometers housed within the compression monitor. For training purposes, the victim shown in FIG. 1 may be replaced by a mannequin, and first aid providers may use the compression monitor to practice abdominal thrusts to learn how hard they must pull to provide an adequate abdominal thrust, and how hard they must pull to provide an excessive abdominal thrust. After training, first aid providers can then perform the abdominal thrusts on actual victims according to the training.

Figure 2:
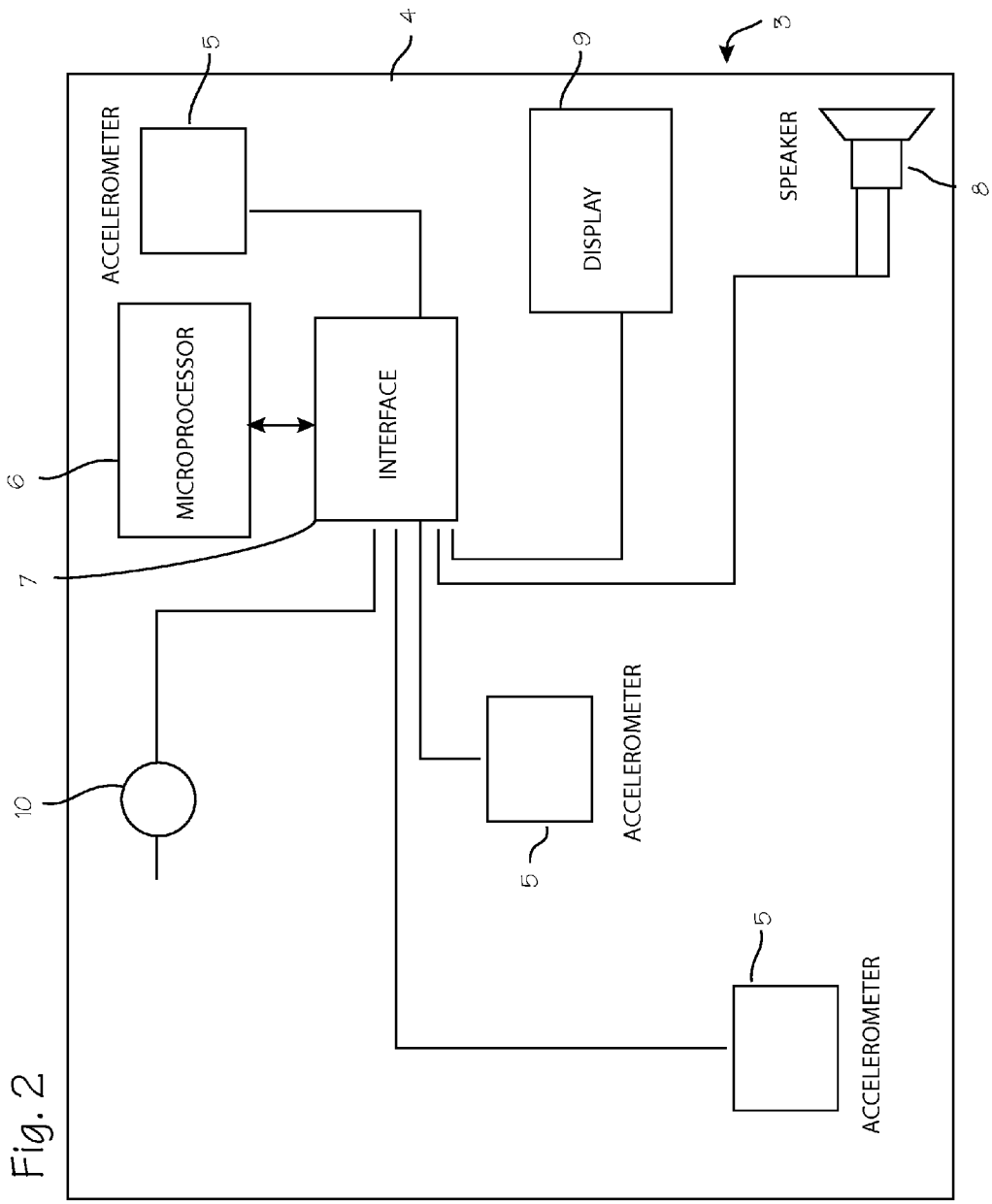
FIG. 2 illustrates the basic layout of a compression monitor.

FIG. 2 illustrates the basic layout of a compression monitor. The compression monitor 3 may take the form of a cell phone, wristwatch, or other ubiquitous device, or may be provided as a stand alone device. Since many cell phones and sport watches now incorporate accelerometers to support other functions, cell phones and sport watches may be adapted to perform the compression monitor function merely by programming them to use the acceleration data from pre-existing accelerometers. The compression monitor includes a housing holding at least one accelerometer for producing an acceleration signal indicative of the displacement of the choking victims abdomen, a microprocessor which is programmed to convert the acceleration signal into a distance value indicative of the displacement of the abdomen caused by abdominal thrust and compare the distance value to a desired range, and then output a signal corresponding to the distance value indicative of the displacement of the abdomen. The output signal can be an audio signal, visual signal, or mechanical signal (a vibration or buzz) perceivable by the first aid provider, and an electronic signal used to record abdominal thrusts. Conveniently, the necessary data can be obtained using the accelerometer alone, without reference to other sensors, using techniques disclosed in U.S. Pat. Nos. 6,390,996, 7,108,665, and 7,429,250. However, the system can be augmented with additional means for detecting the start of an abdominal thrust such as force transducers, force activated switches, and similar mechanisms. The body of the cell phone, wristwatch or dedicated housing of a single purpose device, houses the accelerometers and provides a means for disposing the accelerometer in fixed relation to the first aid providers hands and thus the anterior surface of the victim's abdomen. The signal provided may include voice prompts through a speaker operably connected to the processor or sounds indicative of inadequate movement, adequate movement, and excessive movement of the abdomen, or other prompts. Visible prompts may also be provided, which may be useful for variations of the Heimlich maneuver in which abdominal thrusts are applied from the front of the victim and the device is visible to the rescuer.

In the illustrated implementation, a hand-held abdominal thrust compression monitor 3 comprises a housing 4 which houses a displacement detector comprising one or more accelerometers 5 coupled to a microprocessor 6. The microprocessor can be located in an associated housing. It is most conveniently the onboard microprocessor of a cell phone, sport watch, tablet computer, MP3 player, dedicated compression puck or the like, but may also located in a nearby general purpose computer. The microprocessor is connected to the accelerometer through any suitable interface 7. The signaling mechanism comprises an audible indicator (i.e., a loud speaker) 8, which has an input connected to microprocessor 6 via interface 7. A display 9 may serve as an additional signaling mechanisms for visual signals, and may also be used as a user interface to provide instructions for use and as a touch screen input. A power supply 10 for the various components is preferably located in the housing. The accelerometer is preferably a three-axis accelerometer operable to provide acceleration data to the microprocessor regarding accelerations of three axes (preferably and most conveniently three orthogonal axes) so that movement of the device can be detected regardless of the orientation of the device. The device determines movement along any vector relative to its housing, so that variations in initial placement and orientation do not effect the measured depth of abdominal thrusts. Thus, any tilt in the device is ignored, and this frees the user to hold the device in any convenient orientation. If several three-axis accelerometers are provided in the device, inputs from such a plurality of accelerometers can be interpreted to ensure that the entire housing is moving along the same line, rather than twisting or rotating about a point, which would limit the situations in which rotation of the housing could be misinterpreted as an adequate abdominal thrust.

When implemented on a multi-function device such as a smartphone, the compression monitor function will provided in an app that is active only when opened or activated, such that opening the app or otherwise initiating a mode of operation which monitors for compressions depth causes the microprocessor to analyze input from the accelerometer to accomplish the compression monitoring function. The device, while in this "thrust detection" mode, will monitor the acceleration signal, and interpret any small, slow movements as normal movements, and perhaps provide a persistent low level audio prompt indicating that it is in the thrust detection mode. With constant monitoring of the acceleration signals (which smart phones tend to do in any case to support other functions of the smart phone), the device can detect any abrupt motion and assume that abrupt motion of a certain speed and minimum distance is an intended abdominal thrust, calculate the total distance abruptly moved, compare this to a predetermined desired minimum and maximum values, and then generate an audio signal for annunciation through the speakers which corresponds to the detected movement and how the detected movement compares to the predetermined desired minimum and maximum values. The annunciated sounds can be words ("good compression," "too much" or "too soft" or "good compression" or the like) or sounds of obviously inadequate, adequate, and dangerous character, or sounds arbitrarily assigned and taught to users as an indication of inadequate, adequate and excessive compressions. The minimum and maximum values are programmed into the device, and predetermined at the time of programming.

Figure 3:
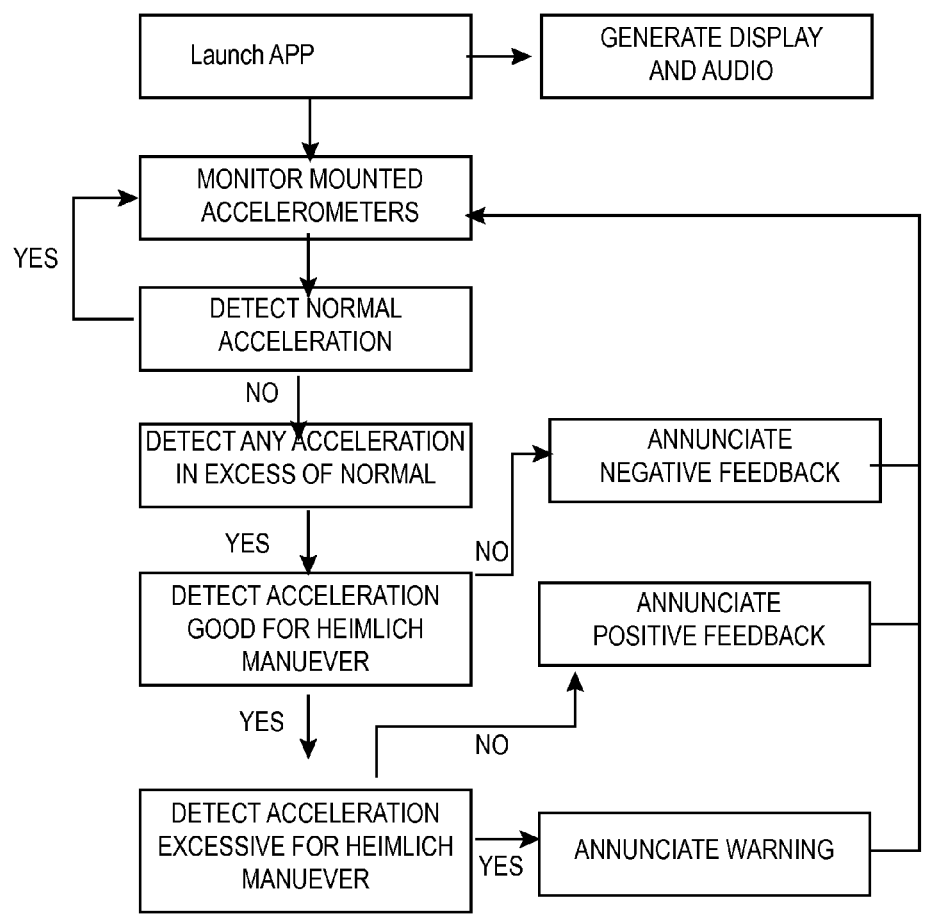
FIG. 3 illustrates the software algorithm applied by a processor to interpret acceleration signals from accelerometers in the compression depth monitor.

FIG. 3 illustrates the software algorithm applied by a processor to interpret acceleration signals from accelerometers in the compression depth monitor. The microprocessor is programmed with software operable on the microprocessor to perform the following method. The method is accomplished through software installed in a device with a microprocessor and the necessary sensors, including accelerometers and, optionally, force sensors (force transducers, force actuated switches, etc.). In a multifunction device such as a smartphone, the software is initiated by launching an application, whereupon the microprocessor operates the device in a compression detecting mode. Once in the compression detecting mode, the microprocessor monitors input from one or more accelerometers to detect acceleration of the device. The device continually monitors the acceleration signals from the accelerometers, and no user input is necessary to indicate that a compression is about to be applied beyond initiation of the application. While monitoring the acceleration signals, the microprocessor may determine that sensed accelerations are nominal, reflecting normal handling and positioning of the device, in which case it merely continues to monitor accelerations without providing feedback, or providing some nominal feedback associated with the monitoring function. If the microprocessor determines that sensed acceleration exceed nominal acceleration, it interprets this as an intended abdominal thrust. If this sensed acceleration or the computed depth and rate of compression are inadequate for an effective application of the Heimlich maneuver, the microprocessor operates the audio speaker or visual display, generating audio output or visual output that communicates to the first aid provider that the abdominal thrust was inadequate. If this sensed acceleration or the computed depth and rate of compression are adequate for an effective application of the Heimlich maneuver, the microprocessor operates the audio speaker or visual display, generating audio output or visual output that communicates to the first aid provider that the abdominal thrust was adequate. If this sensed acceleration or the computed depth and rate of compression are excessive for an effective application of the Heimlich maneuver, the microprocessor operates the audio speaker or visual display, generating audio output or visual output that communicates to the first aid provider that the abdominal thrust was excessive. After any such computation and feedback cycle, the microprocessor programming operates to return the microprocessor to the monitoring function. The method is intended for use in training, in which it will be used to train first aid providers by providing feedback regarding the feel of a proper abdominal thrust and an improper abdominal thrust, so that the first aid provider can duplicate the effort which is indicated as adequate and safe on a mannequin when performing the Heimlich maneuver on a real victim. For systems that can be initialized within a clinical time frame, the method can also be used clinically by first aid providers to guide and record abdominal thrusts applied to real victims.

The device is programmed to compare a measured thrust distance predetermined desired minimum and maximum values, and also compare a predetermined speed, acceleration, or time period over which the thrust is achieved, and indicate to the user that the predetermined acceptable range (between the minimum and maximum values) has been met or exceeded. Currently, the range of acceptable distance for an abdominal thrust is 4 to 5 inches. This should occur over a course of about 0.1 to 0.3 seconds, preferably over about 0.2 seconds (for a average thrust speed of 20 to 25 inches per second). The device is programmed to indicate, upon detection of a thrust meeting these criteria, that the thrust has been adequate and not excessive. The device is programmed to indicate, upon detection of a thrust exceeding these criteria, that the thrust has been excessive. The device may be programmed such that, upon detection of a thrust which fall shorts of the criteria, the device will ignore such thrusts or indicate that the thrust is inadequate (for example, thrusts of 10 to 20 inches per second may be interpreted as intended but inadequate thrusts, while movement at less than 10 inches per second may be interpreted as movement not correlated to an abdominal thrust). The values are determined on the basis of clinical values, and programmed into the device at time of manufacture or through software updated issued from time to time. The values expressed here are the optimum values known to the applicants, but they may be varied as clinical experience dictates.

The computed depth and rate of compression corresponding to nominal movements, abrupt movement that is inadequate for an abdominal thrust, abrupt movement which is adequate, and abrupt movement which is excessive, are:

Nominal speed: up to 20/inches per second;
Intended abdominal thrust: speed in excess of 20/inches per second;
Adequate abdominal thrust: speed in excess of 20/inches per second and total compression of 3-5 inches;
Excessive abdominal thrust: speed in excess of 20/inches per second and total compression in excess of 5 inches.

For administration of the Heimlich maneuver to supine victims, toddlers and infants, these parameters may be adjusted to those considered effective and safe for these special situations. Accelerometers may be mounted on small housings electrically or wirelessly connected to a main device, to address application to infants.

The compression monitor can be operated in a simple mode, in which the method for facilitating the administration of the Heimlich maneuver on a choking victim uses the compression monitor to detect the depth of an abdominal thrusts while performing an abdominal thrust and merely reports the depth obtained. This method uses the compression monitor as described above, including the microprocessor operably connected to the accelerometer, with the microprocessor programmed to convert the acceleration signal into a distance value indicative of the displacement of the mannequin's abdomen or the choking victim's abdomen caused by abdominal thrusts and further programmed to compare the distance value to a set range. The microprocessor is also programmed to operate the signaling mechanism operably connected to the microprocessor, when the distance value is within the desired range and/or when the distance value exceed the desired range, to provide corresponding prompts to the rescuer. The accelerometers measure the acceleration and generate an acceleration signal, and the microprocessor receives the acceleration signal and calculates an abdominal compression displacement signal corresponding to the distance the abdomen is compressed by the administration of the abdominal thrust, and provides a signal corresponding to the distance value indicative of the depth of the abdominal thrust to generate an output to the user.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A method of training first aid providers in the application of the Heimlich maneuver to a choking victim, said method comprising:
   providing a compression monitor, comprising: an accelerometer, a signaling mechanism and a microprocessor, operable to receive and interpret acceleration signals from the accelerometer and operate the signaling mechanism, to provide feedback to a first aid provider;
   wherein the microprocessor is further programmed to convert the acceleration signals into a distance value indicative of displacement of an abdominal area of a mannequin caused by an abdominal thrust, compare the distance value to a desired range, and operate the signaling mechanism to indicate when the distance value is within the desired range;
   wherein the desired range is 4 to 5 inches;
   securing the compression monitor to a portion of the first aid provider's hand or wrist which remains in substantially fixed relation to a surface of the mannequin's abdominal area which is to be compressed;
   operating the compression monitor to determine depth of the abdominal thrust performed by the first aid provider;
   performing an abdominal thrust on the mannequin; and
   providing feedback to the first aid provider indicating adequacy of the abdominal thrust.

2. A method of guiding first aid providers in the application of the Heimlich maneuver to a choking victim, said method comprising:
   providing a compression monitor, comprising: an accelerometer, a signaling mechanism and a microprocessor, operable to receive and interpret acceleration signals from the accelerometer and operate the signaling mechanism, to provide feedback to a first aid provider;
   wherein the microprocessor is further programmed to convert the acceleration signals into a distance value indicative of displacement of an abdominal area of the choking victim caused by an abdominal thrust, compare the distance value to a desired range, and operate the signaling mechanism to indicate when the distance value is within the desired range;
   wherein the desired range is 4 to 5 inches;
   securing the compression monitor to a portion of the first aid provider's hand or wrist which remains in substantially fixed relation to a surface of the victim's abdominal area which is to be compressed;
   operating the compression monitor to determine depth of the abdominal thrust performed by the first aid provider;
   performing an abdominal thrust on the choking victim; and
   providing feedback to the first aid provider indicating adequacy of the abdominal thrust.

3. The method of claim 1, where the microprocessor is further programmed to determine speed of movement of the compression monitor, and, for thrusts measured at over 20 inches per second, operate the signaling mechanism to indicate that the distance value is within the desired range.

4. The method of claim 2, where the microprocessor is further programmed to determine speed of movement of the compression monitor, and, for thrusts measured at over 20 inches per second, operate the signaling mechanism to indicate that the distance value is within the desired range.

5. A method of training first aid providers in the application of the Heimlich maneuver to a choking victim, said method comprising:

provuiding a compression monitor, comprising: an accelerometer, a signaling mechanism and a microprocessor, operable to receive and interpret acceleration signals from the accelerometer and operate the signaling mechanism, to provide feedback to a first aid provider;

wherein the microprocessor is further programmed to convert the acceleration signals into a distance value indicative of displacement of an abdominal area of a mannequin caused by an abdominal thrust, compare the distance value to a desired range, and operate the signaling mechanism to indicate when the distance value is outside the desired range;

wherein the desired range is 4 to 5 inches;

securing the compression monitor to a portion of the first aid provider's hand or wrist which remains in substantially fixed relation to a surface of the mannequin's abdominal area which is to be compressed;

operating the compression monitor to determine depth of the abdominal thrust performed by the first aid provider;

performing an abdominal thrust on the mannequin; and providing feedback to the first aid provider indicating adequacy of the abdominal thrust.

6. The method of claim 5, where the microprocessor is further programmed to determine speed of movement of the compression monitor, and, for thrusts measured at over 20 inches per second, operate the signaling mechanism to indicate that the distance value is outside the desired range.

7. A method of training first aid providers in the application of the Heimlich maneuver to a choking victim, said method comprising:

providing a compression monitor, comprising: an accelerometer, a signaling mechanism and a microprocessor, operable to receive and interpret acceleration signals from the accelerometer and operate the signaling mechanism, to provide feedback to a first aid provider;

wherein the microprocessor is further programmed to convert the acceleration signals into a distance value indicative of displacement of an abdominal area of a choking victim caused by an abdominal thrust compare the distance value to a desired range, and operate the signaling mechanism to indicate when the distance value is outside the desired range;

wherein the desired range is 4 to 5 inches;

securing the compression monitor to a portion of the first aid provider's hand or wrist which remains in substantially fixed relation to a surface of the choking victim's abdominal area which is to be compressed;

operating the compression monitor to determine depth of the abdominal thrust performed by the first aid provider;

performing an abdominal thrust on the choking victim; and providing feedback to the first aid provider indicating adequacy of the abdominal thrust.

8. The method of claim 7, where the microprocessor is further programmed to determine speed of movement of the compression monitor, and, for thrusts measured at over 20 inches per second, operate the signaling mechanism to indicate that the distance value is outside the desired range.

* * * * *